US008846759B2

(12) United States Patent
Luiking et al.

(10) Patent No.: US 8,846,759 B2
(45) Date of Patent: Sep. 30, 2014

(54) LOW-CALORIC HIGH-PROTEIN NUTRITIONAL COMPOSITION FOR THE STIMULATION OF MUSCLE PROTEIN SYNTHESIS

(75) Inventors: Yvette Charlotte Luiking, Venray (NL); George Verlaan, Wageningen (NL); Marion Jourdan, Arnhem (NL)

(73) Assignee: N.V. Nutricia (NL)

( * ) Notice: Subject to any disclaimer, the term of this patent is extended or adjusted under 35 U.S.C. 154(b) by 45 days.

(21) Appl. No.: 13/518,281

(22) PCT Filed: Dec. 23, 2010

(86) PCT No.: PCT/NL2010/050887
§ 371 (c)(1),
(2), (4) Date: Mar. 20, 2013

(87) PCT Pub. No.: WO2011/078677
PCT Pub. Date: Jun. 30, 2011

(65) Prior Publication Data
US 2013/0203658 A1  Aug. 8, 2013

(30) Foreign Application Priority Data
Dec. 24, 2009  (WO) ................ PCT/NL2009/050806

(51) Int. Cl.
| | |
|---|---|
| A61K 35/20 | (2006.01) |
| A23L 1/304 | (2006.01) |
| A23L 1/305 | (2006.01) |
| A23L 1/29 | (2006.01) |
| A61K 31/70 | (2006.01) |
| A61K 35/74 | (2006.01) |
| A61K 38/17 | (2006.01) |
| A23L 1/302 | (2006.01) |
| A23L 1/308 | (2006.01) |

(52) U.S. Cl.
CPC ................ *A23L 1/296* (2013.01); *A23L 1/304* (2013.01); *A23L 1/3056* (2013.01); *A61K 31/70* (2013.01); *A61K 35/74* (2013.01); *A23L 1/3051* (2013.01); *A61K 38/1709* (2013.01); *A23L 1/302* (2013.01); *A23L 1/308* (2013.01)
USPC ......................................................... 514/561

(58) Field of Classification Search
None
See application file for complete search history.

(56) References Cited

U.S. PATENT DOCUMENTS

2004/0122097 A1* 6/2004 Verlaan et al. ................ 514/561

FOREIGN PATENT DOCUMENTS

| WO | 2004056208 A1 | 7/2004 |
|---|---|---|
| WO | 2007043870 A1 | 4/2007 |
| WO | 2011078677 A3 | 6/2011 |

OTHER PUBLICATIONS

Koopman et al ("Combined ingestion of protein and free leucine with carbohydrate increases postexercise muscle protein synthesis in vivo in male subjects" (2004) Am J Physiol Endocrinol Metab 288: E645-E653).*
Volek ("Leucine triggers muscle growth" Nutrition Express. downloaded from http://www.nutritionexpress.com/article+index/protein/showarticle.aspx?id=807 on Oct. 18, 2013).*
Youdim ("Essential Fatty acids and the brain: possible health implications." Int. J Devl. Neuroscience (2000) 18: 383-399.*
Koopman et al (Am J Physiol Endocrinol Metab (2004) 288: E645-E653).*
Youdim (Int J Dev Neurosci (2000) 18: 383-399).*
Wikipedia "Milk" http://en.wikipedia.org/wiki/Milk, downloaded May 13, 2014.*
Anthony, et al., "Leucine Stimulates Translation Initiation in Skeletal Muscle of Postabsorptive Rats via a Rapamycin-Sensitve Pathway", J Nutr, 2000, pp. 2413-2419.
Bartali, et al., "Low Nutrient Intake is an Essential Component of Frailty in Older Persons", J Gerontol Biol Sci Med Sci, 2006, pp. 589-593, vol. 61A.
Bischoff-Ferrari, et al., "Higher 25-Hydroxyvitamin D Concentrations are Associated with Better Lower-Extremity Function in both Active and Inactive Persons Aged > or =60y", Am J Clin Nutr, 2004, pp. 752-758.
Bischoff-Ferrari, et al., "Prevention of Nonvertebral Fractures with Oral Vitamin D and Dose Dependency: A Meta-Analysis of Randomized Controlled Trials", Arch Intern Med, 2009, pp. 551-561.
Bohe, et al., "Human Muscle Protein Synthesis is Modulated by Extracellular, not Intramuscular Amino Acid Availability: A Dose-Response Study", J Physiol, 2003, pp. 315-324.

(Continued)

*Primary Examiner* — Karlheinz R Skowronek
*Assistant Examiner* — Mindy Newman
(74) *Attorney, Agent, or Firm* — Banner & Witcoff, Ltd.

(57) ABSTRACT

The present invention relates to the use of a low-caloric high-protein nutritional composition for use in the prevention or treatment of a disease or condition in a mammal, which involves muscle decline, as well as to specific low-caloric high-protein nutritional compositions for stimulating muscle protein synthesis in a mammal. In particular, the invention relates to the use of a nutritional composition comprising per 100 kcal: (i) at least about 12 g of proteinaceous matter which comprises at least about 80 weight % of whey protein, relative to the total proteinaceous matter, and which comprises at least about 11 weight % of leucine, relative to the total proteinaceous matter, of which at least about 20 weight % is in a free form, relative to the total leucine, (ii) a source of fat and a source of digestible carbohydrates, for the prevention or treatment of a disease or condition which involves muscle decline in a mammal, especially an elderly mammal, wherein the nutritional composition is administered as 1 to 2 servings daily, each serving comprising between 80 and 200 kcal.

40 Claims, 4 Drawing Sheets

(56) References Cited

OTHER PUBLICATIONS

Boirie, et al., "Slow and Fast Dietary Proteins Differently Modulate Postprandial Protein Accretion", Proc Natl Acad Sci USA, 1997, pp. 14930-14935.

Boirie, et al., "Splanchnic and Whole-Body Leucine Kinetics in Young and Elderly Men", Am J Clin Nutr, 1997, pp. 489-495.

Boirie, et al., "Physiopathological Mechanism of Sarcopenia", J Nutr Health Aging, 2009, pp. 717-723.

Clarkston, et al., "Evidence for the Anorexia of Aging: Gastrointestinal Transit and Hunger in Healthy Elderly vs. Young Adults", Am J Physiol, 1997, pp. R243-R248.

Cuthbertson, et al., "Anabolic Signaling Deficits Underlie Amino Acid Resistance of Wasting, Aging, Muscle", FASEB J, 2004, pp. 422-424.

Dangin, et al., "The Digestion Rate of Protein is an Independent Regulating Factor of Postprandial Protein Retention", Am J Physiol Endocrinol Metab, 2001, pp. E340-E348.

Dangin, et al., "Influence of the Protein Digestion Rate on Protein Turnover in Young and Elderly Subjects", J Nutr, 2002, pp. 3228S-3233S.

Dangin, et al. "The Rate of Protein Digestion Affects Protein Gain Differently During Aging in Humans", J Physiol, 2003, pp. 635-644.

Guillet, et al., "Impaired Anabolic Response of Muscle Protein Synthesis is Associated with S6K1 Dysregulation in Elderly Humans", FASEB J, 2004, pp. 1586-1587.

Holick, Michael F., "Vitamin D Deficiency", N Engl J Med, 2007, pp. 266-281.

Katsanos, et al., "Aging is Associated with Diminished Accretion of Muscle Proteins After the Ingestion of a Small Bolus of Essential Amino Acids", Am J Clin Nutr, 2005, pp. 1065-1073.

Katsanos, et al., "A High Proportion of Leucine is Required for Optimal Stimulation of the Rate of Muscle Protein Synthesis by Essential Amino Acids in the Elderly", Am J Physiol Endocrinol Metab, 2006, pp. E381-E387.

Lesser, et al., "Nutritional Situation of the Elderly in Eastern/Baltic and Central/Western Europe—The Ageing Nutrition Project", Ann Nutr Metab, 2008, pp. 62-71.

Marzani, et al., "Antioxidant Supplementation Restores Defective Leucine Stimulation of Protein Synthesis in Skeletal Muscle from Old Rats", J Nutr, 2008, pp. 2205-2211.

Paddon-Jones, et al., "Amino Acid Ingestion Improves Muscle Protein Synthesis in the Young and Elderly", Am J Physiol Endocrinol Metab, 2003, pp. E321-E328.

Paddon-Jones, et al., "Differential Stimulation of Muscle Protein Synthesis in Elderly Humans Following Isocaloric Ingestion of Amino Acids or Whey Protein", Exp Gerontol, 2006, pp. 215-219.

Rasmussen, et al., "Insulin Resistance of Muscle Protein Metabolism in Aging", FASEB J, 2006, pp. 768-769.

Rieu, et al., "Leucine Supplementation Improves Muscle Protein Synthesis in Elderly Men Independently of Hyperaminoacidaemia", J Physiol, 2006, pp. 305-315.

Rieu, et al., "Increased Availability of Leucine with Leucine-Rich Whey Proteins Improves Postprandial Muscle Protein Synthesis in Aging Rats", Nutrition, 2007, pp. 323-331.

Rolland, et al., "Sarcopenia: Its Assessment, Etiology, Pathogenesis, Consequences and Future Perspectives", J Nutr Heath Aging, 2008, pp. 433-450.

Semba, et al., "Low Serum Micronutrient Concentrations Predict Frailty Among Older Women Living in the Community", J Gerontol A Biol Sci Med Sci, 2006, pp. 594-599.

Seshadri, et al., "Plasma Homocysteine as a Risk Factor for Dementia and Alzheimer's Disease", N Engl J Med, 2002, pp. 476-483.

Short, et al., "Mechanisims of Sarcopenia of Aging", J Endocrinol Invest, 1999, pp. 95-105.

Volpi, et al., "Exogenous Amino Acids Stimulate Net Muscle Protein Synthesis in the Elderly", J Clin Invest, 1998, pp. 2000-2007.

Volpi, et al., "Oral Amino Acids Stimulate Muscle Protein Anabolism in the Elderly Despite Higher First-Pass Splanchnic Extraction", Am J Physiol, 1999, pp. E513-E520.

Volpi, et al., "Essential Amino Acids are Primarily Responsible for the Amino Acid Stimulation of Muscle Protein Anabolism in Healthy Elderly Adults", 2003, pp. 250-258.

World Health Organization, "Keep Fit for Life: Meeting the Nutritional Needs of Older Persons", 2002.

Wolfe, Robert R., "Protein Supplements and Exercise", Am J Clin Nutr., 2000, pp. 551S-557S.

H A Biscoff-Ferrari, et al., "Fall Prevention with Supplemental and Active Forms of Vitamin D: A Meta-Analysis of Randomized Controlled Trials", BMJ, 2009, pp. 1-11.

Anonymous: "Cocoa Powder", Swiss Food Composition Database, Mar. 3, 2014, vol. 5.0 XP055105138, Retrieved from the Internet: URL:http://naehrwertdaten.ch/request query=ProductDetails &xml=MessageData&xml=MetaData&pdf=PdfOutput &productId=7206&lan=en&pageKey=Pdf [retrieved on Mar. 3, 2014].

Walter et al., "Cocoa powder Oil partially Removed", Food Composition and Nutrition Tables, Medpharm Scientific Publishers, Jan. 1, 2000, pp. 1113, XP002696871, Stuttgart, Germany, ISBN: 978-3-88763-076-8.

Office Action Rule 71(3) dated Jul. 8, 2014 in the corresponding EP application 10 807 402.2-1405.

\* cited by examiner

LOW-CALORIC HIGH-PROTEIN NUTRITIONAL COMPOSITION FOR THE STIMULATION OF MUSCLE PROTEIN SYNTHESIS

RELATED APPLICATION DATA

This application is a National Stage Application under 35 U.S.C. 371 of co-pending PCT application PCT/NL2010/050887 designating the United States and filed Dec. 23, 2010; which claims the benefit of PCT application PCT/NL2009/050806 and filed Dec. 24, 2009 each of which are hereby incorporated by reference in their entireties.

FIELD OF THE INVENTION

The present invention relates to the use of a low-caloric high-protein nutritional composition suitable for the prevention or treatment of a disease or condition in a mammal, which involves muscle decline, as well as to specific low-caloric high-protein nutritional compositions suitable for stimulating muscle protein synthesis in a mammal.

BACKGROUND OF THE INVENTION

Age-related involuntary loss of muscle mass and strength occurs during ageing and is called sarcopenia [1]. Regarding the degenerative loss of skeletal muscle mass, it occurs at a rate of 3-8% per decade after the age of 30 years and accelerate from 60 years of age. Both impaired muscle mass and muscle strength relate to age-related loss of muscle function.

The major drivers for maintenance of skeletal muscle mass are the stimulation of muscle protein synthesis and the inhibition of muscle protein breakdown. Muscle protein synthesis is stimulated by the bioavailability of amino acids (in particular of leucine) and physical activity.

Hence, both contribute to a positive net muscle protein balance (i.e. difference between muscle protein synthesis and protein breakdown; net muscle protein synthesis). It is important to maintain muscle mass and prevent muscle decline and muscle wasting. Protein starvation and muscle inactivity, which often occur with ageing and disease, result in a failure to maintain muscle mass, with muscle wasting. With ageing, an imbalance exists between muscle protein synthesis and breakdown. Moreover, the anabolic response to feeding decreases, which further contributes to an insufficient net muscle protein synthesis, and subsequent muscle decline with ageing. [1-6]. Compared to younger adults, elderly need higher levels of blood amino acids—especially leucine—to stimulate muscle protein synthesis. This phenomenon of reduced responsiveness of muscle that occurs in elderly, is called anabolic resistance which leads to muscle decline. Hence, it is beneficial to have a nutritional composition, especially for elderly, to overcome this resistance and stimulate (net) muscle protein synthesis. Indeed, a so called "fast" protein source with high leucine proved more effective in elderly than a similar protein amount with low leucine or a "slow" protein [7, 8]. Thus, an adequate anabolic stimulus to the muscle still has the potential to activate the muscle protein signalling pathway and thereby provoke muscle protein synthesis in a mammal, especially in an elderly mammal.

Specific amino acids are known for their stimulating effect on muscle protein synthesis; these amino acids are considered "anabolic". Of the amino acids, essential amino acids (EAAs) in particular are able to stimulate muscle protein synthesis in the elderly, whereas non-EAAs may be of less benefit for muscle anabolism [9, 10]. Elderly require a higher dose of EAAs (>6.7 g EAAs), provided as a bolus, to stimulate muscle anabolism [11, 12]. Hence, the age-related lower responsiveness could also be overcome by increasing leucine intake (from 1.7 g to 2.8 g leucine in a mixture of 6.7 g EAAs) [8]. Leucine also acts as a signalling molecule [13]. The importance of leucine for muscle protein synthesis was also confirmed for intact protein sources with various levels of leucine (whey sources and casein) in an animal study. In this study, old rats showed a gradual increase in muscle protein synthesis concomitant with an increase of leucine level in the protein source, as is the case for whey protein [14]. In healthy elderly, whey protein also resulted in a higher whole body protein synthesis rate compared with casein protein [15].

Muscle protein synthesis is positively related to the extracellular amino acid concentration [16] and intracellular amino acid appearance in the muscle [17]. An increase in serum amino acid concentration may stimulate muscle protein synthesis, but higher levels of essential amino acids and especially leucine, are needed in the elderly [8, 11]. Therefore, strategies that can significantly increase blood leucine levels seem useful to help restore the acute anabolic response to feeding in elderly. Blood amino acid levels after feeding can be influenced by the type of food. Part of the dietary amino acids is extracted in the intestine and liver for local protein synthesis (i.e. splanchnic extraction or sequestration). The remaining amino acids appear in the systemic blood circulation and reach other organs, with the muscle as the largest protein reservoir [18]. Dietary proteins vary in amino acid composition, in rate of digestion, and in level of splanchnic extraction, all influencing the subsequent appearance of amino acids in the circulation. Because whey protein contains higher levels of leucine than casein protein, serum leucine levels are higher after intake of whey protein [15]. Previous studies comparing casein protein and whey protein identified casein as a "slow" protein and whey as a "fast" protein, referring to the rate of appearance in the circulation of the amino acids [7, 19]. The digestion rate is an important factor in this slow/fast concept [20] and is partly determined by the rate of gastric emptying. In elderly, the appearance of amino acids in the blood is reduced [15], because splanchnic extraction is higher [21, 22] and digestion/gastric emptying rate is slower [23] than in young.

Following the need for supplying higher levels of amino acids to increase the bioavailability of anabolic amino acids to stimulate muscle protein synthesis in a mammal, especially in an elderly human, serum amino acid levels in elderly after intake of a high whey-protein containing, low-caloric nutritional formulations were studied. The clinical study evaluated the bioavailability of amino acids in elderly after intake of such a nutritional formulation.

SUMMARY DESCRIPTION OF THE INVENTION

Surprisingly, the inventors found that essential amino acids, in particular leucine, showed an improved bioavailability of amino acids to stimulate muscle protein synthesis and subsequent muscle mass by using a new, low-caloric high-protein nutritional formulation. Without being bound by theory, it is hypothesized that amino acids reach the circulation faster and reach higher blood levels when dietary protein is given in a low-caloric composition compared to a high-caloric composition, preferably using whey, although the effect is the same but smaller for casein. In the course of this application, this effect will be called the low energy-effect. This low-energy effect could beneficially be used for treatment of persons suffering from any disease or condition, the prevention and treatment of which is related to the synthesis of muscle protein, in particular, sarcopenia, a disease which involves muscle decline with insufficient (net) muscle protein synthesis and muscle decline, associated with aging.

DETAILED DESCRIPTION OF THE INVENTION

According to one aspect, the present invention is concerned with a nutritional composition comprising per 100 kcal:
(i) at least about 12 g of proteinaceous matter which comprises at least about 80 weight % of whey protein, relative to the total proteinaceous matter, and which comprises at least about 11 weight % of leucine, relative to the total proteinaceous matter, of which at least about 20 weight % is in a free form, relative to the total leucine,
(ii) a source of fat and a source of digestible carbohydrates, for use in the prevention or treatment of a disease or condition which involves muscle decline in a mammal, wherein the nutritional composition is administered as 1 to 2 servings daily, each serving comprising between 80 and 200 kcal.

In the context of this application, the term "at least" also includes the starting point of the open range. For example, an amount of "at least 95 weight %" means any amount equal to 95 weight % or above.

In the context of this application, the term "about" means a deviation of 5% or less from the given value, such as 4%, 3%, 2%, 1%, or less than 1%. For example, an amount of "about 12 g" means any amount equal to 12 g±0.6 g, i.e. any amount in the range of 11.4 to 12.6 g. The reason for the use of the term "about" is to take into account the uncertainty associated with the detection method, or the variability of the manufacturing method when it concerns the manufacturing of a nutritional composition.

In the context of this application, the term "or" is defined as "and/or" unless specified otherwise. Hence, the wording "A or B" comprises the individual members A and B, as well as the combined members A and B.

In the context of this application, the wording "a", "an" and "the" imply both the singular as the plural of the noun to which it refers. Hence, the wording "a protein" means one or more proteins.

Proteinaceous Matter

The nutritional composition according to the invention comprises at least about 12 g of proteinaceous matter per 100 kcal. With the term "proteinaceous matter" is meant a protein or any part of a protein, such as but not limited to non-hydrolyzed protein, native protein, hydrolyzed protein, peptides, such as oligopeptides and dipeptides, and amino acids. Preferably, the proteinaceous matter originates from dairy proteins, such as whey and casein. The amino acids are essentially L-amino acids as only L-amino acids are metabolically available.

Preferably, the composition comprises at least about 12.5 g, at least about 13 g, at least about 13.5 g, and most preferably about 14 g of proteinaceous matter per 100 kcal.

According to another embodiment, the nutritional composition according to the invention comprises at least about 48 en % of proteinaceous matter per 100 kcal. Preferably, the composition comprises at least about 50 en %, at least about 52 en %, at least about 54 en %, and most preferably about 56 en % of proteinaceous matter per 100 kcal.

The proteinaceous matter according to the invention comprises at least about 80 weight % of whey protein, preferably at least about 85 weight % of whey protein, preferably at least about 90 weight %, and most preferably about 95 weight % of whey protein.

As discussed above, whey protein is considered a "fast" protein referring to the rate of appearance in the circulation of the amino acids. The whey protein may be an intact whey protein, a hydrolysed whey protein, a microparticular whey protein, a nanoparticular whey protein, a micellar whey protein, and the like. Preferably, the whey protein is an intact-whey protein, i.e. a whey protein in its intact form, such as present in fresh milk. Hydrolysed whey protein suffers from the drawback that it has an unpleasant taste.

As a source of whey protein to be used in the present invention, any commercially available whey protein source may be used, i.e. whey obtained by any process for the preparation of whey known in the art, as well as whey protein fractions prepared thereof, or the proteins that constitute the bulk of the whey proteins being β-lactoglobulin, α-lactalbumin and serum albumin, such as liquid whey, or whey in powder form, such as whey protein isolate (WPI) or whey protein concentrate (WPC). Whey protein concentrate is rich in whey proteins, but also contains other components such as fat, lactose and glycomacroprotein (GMP), a casein-related non-globular protein. Typically, whey protein concentrate is produced by membrane filtration. On the other hand, whey protein isolate consists primarily of whey proteins with minimal amounts of fat and lactose. Whey protein isolate usually requires a more rigorous separation process such as a combination of microfiltration and ultra-filtration or ion exchange chromatography. It is generally understood that a whey protein isolate refers to a mixture in which at least 90 weight % of the solids are whey proteins. A whey protein concentrate is understood as having a percentage of whey proteins between the initial amount in the by-product (about 12 weight %) and a whey protein isolate. In particular, sweet whey, obtained as a by-product in the manufacturing of cheese, acid whey, obtained as a by-product in the manufacturing of acid casein, native whey, obtained by milk microfiltration or rennet whey, obtained as a by-product in the manufacturing of rennet casein, may be used as a source of whey proteins.

Furthermore, whey proteins may originate from all kinds of mammalian animal species, such as, for instance cows, sheep, goats, horses, buffalo's, and camels. Preferably, the whey protein is of bovine origin.

Preferably, the whey protein source is available as a powder, preferably the whey protein source is a WPC or WPI.

According to another embodiment, the proteinaceous matter according to the invention comprises at least about 45 weight % of essential amino acids (EAA), preferably at least about 47 weight %, and more preferably at least about 50 weight % of EAA. Essential amino acids are amino acids selected from the group of isoleucine (Ile), leucine (Leu), lysine (Lys), methionine (Met), phenylalanine (Phe), threonine (Thr), tryptophan (Trp), and valine (Val).

Since native whey protein comprises maximum (depending on the source) about 45 weight % of EAA, it may be necessary to add EAA's to the nutritional composition, such as in the form of amino acids or peptides. It was found that about 45 weight % of total EAA is a minimum amount present in the nutritional composition.

The proteinaceous matter according to the invention comprises at least about 11 weight % of leucine. Since natural whey protein comprises maximum (depending on the source) about 11 weight % of leucine, it may be necessary to add leucine to the nutritional composition, such as in the form of amino acids or peptides. It was found that about 11 weight % of total leucine is a minimum amount present in the nutritional composition.

Preferably, the proteinaceous matter according to the invention comprises at least about 12 weight %, preferably at least about 12.5 weight %, more preferably at least about 13 weight % of leucine, most preferably at least about 14 weight % of leucine.

Total leucine comprises at least about 20 weight %, preferably at least about 22.5 weight %, preferably at least about 26 weight % of leucine in a free form, relative to the total amount of leucine. Total leucine comprises at most about 70 weight %, preferably at most about 60%, preferably at most about 50% of leucine in a free form, relative to the total amount of leucine. With "free form" is meant a peptide comprising 1 to 5 amino acids, preferably 1 to 3 amino acids, more preferably 1 amino acid. Preferably, leucine is a free amino acid, either as a base, a salt or a chelate.

According to another embodiment, the proteinaceous matter according to the invention comprises a total amount of leucine, valine and isoleucine in a leucine:valine:isoleucine ratio of about 1.7-3:1:1. Alternatively, the weight ratio of leucine:(valine+isoleucine) is about 0.9 or higher, preferably 1.0 or higher. Suitable valine and isoleucine levels may be provided by the whey protein, or may be provided by added amino acids, either in free form as bases or salts, or as peptides.

Fat and Carbohydrates

The low-caloric nutritional composition according to the invention should comprise a source of fat and a source of carbohydrates. The presence of these components prohibits the excessive use of the protein as an energy source instead of for stimulating muscle protein synthesis.

The total amount of energy supplied by the fat and carbohydrates (digestible and indigestible) should match the total energy supplied by the proteinaceous matter. Therefore, the total amount fat and carbohydrates per 100 kcal should be at most about 52 en %, in particular at most about 50 en %, preferably at most about 48 en %, more preferably at most about 46 en %, or about 44 en %.

The amount of energy supplied by respectively the fat and the carbohydrates may vary within wide limits, as long as both components are present. According to one embodiment, the amount of fat may vary between 10 and 35 en %, preferably between 15 and 30 en %. According to one embodiment, the amount of carbohydrate may vary between 10 and 35 en %, preferably between 15 and 30 en %. According to one embodiment, the sum of the amounts of fat and carbohydrate may range between 10 and 60 en %.

In a preferred embodiment, the nutritional composition according to the invention comprises about 2 g of fat and about 6.2 to about 6.4 g of digestible carbohydrates per 100 kcal.

In a further preferred embodiment, the nutritional composition according to the invention comprises about 2 g of fat and about 6.4 g of digestible carbohydrates per 100 kcal.

With regard to the type of fat, a wide choice is possible, as long as the fat is of food quality.

The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. In one embodiment, the present composition comprises rapeseed oil, corn oil or sunflower oil. The fat may include a source of medium chain fatty acids (mainly 8 to 10 carbon atoms long), such as medium chain triglycerides (MCT), a source of long chain fatty acids (mainly at least 18 carbon atoms long), such as poly-unsaturated fatty acids (PUFA's) as omega-3 and omega-6 fatty acids, including EPA, DHA and long chain triglycerides (LCT), and phospholipid-bound fatty acids such as phospholipid-bound, EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body. Independent of the anti-inflammatory properties of omega-3 fatty acids, omega-3 fatty acids, such as EPA and DHA, may stimulate muscle protein synthesis by increasing muscle anabolic signaling activity. Hence, according to a preferred embodiment, the source of fat comprises omega-3 fatty acids, in particular EPA and DHA.

With regard to the type of carbohydrates, a wide choice is possible, as long as the carbohydrates are of food quality. The digestible carbohydrates positively influence the energy level of a subject, and add to the advantageous effect of the nutritional composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and polysaccharides.

The liquid enteral nutritional composition according to the invention may optionally be fortified with dietary fibres (or prebiotics fibres) such as non-digestible carbohydrates such as galacto-oligosaccharides, fructo-oligosaccharides, inulin, and pectin (hydrolysed pectin, low-viscosity pectin (a pectin degradation product with a DP of 2-250), or other pectin degradation products). In an embodiment of the present invention, the composition according to the invention comprises 0.5 g/100 kcal to 6 g/100 kcal of non-digestible carbohydrates. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylo-oligosaccharides (XOS), soy oligosaccharides, and the like. Optionally, also higher molecular weight compounds such as inulin, soy polysaccharides, acacia polysaccharides (acacia fibre or arabic gum), cellulose, resistant starch and the like may be incorporated in the composition according to the invention. The amount of insoluble fibre such as cellulose is preferably lower than 20 weight % of the dietary fibre fraction of the composition according to the invention, or below 0.6 g/100 kcal. The amount of thickening polysaccharides such as carrageenans, xanthans, pectins, galactomannans and other high molecular weight (DP>50) indigestible polysaccharides is preferably low, i.e. less than 20% of the weight of the fibre fraction, or less than 1 g/100 kcal. Instead, hydrolysed polysaccharides such as hydrolysed pectins and galactomannans can advantageously be included.

A preferred fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructo-oligosaccharides or galacto-oligosaccharides (GOS), which may also contain a small amount of higher saccharides (e.g. with a DP of 11 to 20). Such oligosaccharides preferably comprise 50 weight % to 90 weight % of the fibre fraction, or 0.5 g/100 kcal to 3 g/100 kcal of the composition according to the invention. Other suitable fibre components include saccharides that have only partial digestibility.

In a particular embodiment, the composition according to the invention comprises one or more of fructo-oligosaccharides, inulin, acacia polysaccharides, soy polysaccharides, cellulose and resistant starch.

In another embodiment of the present invention, the composition according to the invention may comprise a mixture of neutral and acid oligosaccharides as disclosed in WO 2005/039597 (N.V. Nutricia), which is incorporated herein by reference in its entirety. More in particular, the acid oligosaccharide has a degree of polymerization (DP) between 1 and 5000, preferably between 1 and 1000, more preferably between 2 and 250, even more preferably between 2 and 50, most preferably between 2 and 10. If a mixture of acid oligosaccharides with different degrees of polymerization is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparin, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterized by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterized by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day.

The term neutral oligosaccharides as used in the present invention refers to saccharides which have a degree of polymerization of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerization of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, D-galactopyranose, ribose, glucose, xylose and derivatives thereof, calculated on the total number of monose units contained therein. Suitable neutral oligosaccharides are preferably fermented by the gut flora. Preferably, the oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), pa nose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxohexulose, lactosucrose (O-β-D-galactopyranosyl-(1-4)-O-α-D-glucopyranosyl-(1-2)-β-D-fructofuranoside), α-galactooligosaccha rides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4) α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactose I, II and III), fructans—Levan-type (β-D-(2→6)-fructofuranosyl)$_n$ α-D-glucopyranoside), fructans—Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosacchararides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of Bi. adolescentis. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment, the composition according to the invention comprises an acid oligosaccharide with a DP between 2 and 250, prepared from pectin (such as hydrolysed pectin (an acid oligosaccharide (AOS)) and low-viscosity pectin), alginate, and mixtures thereof; and a neutral oligosaccharide, selected from the group of fructans, fructooligosaccharides, indigestible dextrins, galactooligosaccharides including transgalactooligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect. Preferably the composition according to the invention comprises:

- an acid oligosaccharides as defined above (preferably low-viscosity pectin);
- a galactose-based neutral oligosaccharide (of which more than 50% of the monose units are galactose units), preferably selected from the group consisting of galactooligosaccharide and transgalactooligosaccharide; and
- a fructose or glucose based neutral oligosaccharide (of which more than 50% of the monose units are fructose or glucose, preferably fructose units), preferably inulin, fructan or fructooligosaccharide, most preferably long chain fructooligosaccharide (with an average DP of 10 to 60).

Preferably, the nutritional composition further comprises one or more dietary fibres selected from the group of short chain GOS, long chain FOS, inulin and low-viscosity pectin.

In a particular preferred embodiment, the nutritional composition comprises per 100 kcal:
  (ii) about 14 g of proteinaceous matter which comprises about 95 weight % of whey protein, relative to the total proteinaceous matter, and which comprises at least about 14 weight % of leucine, relative to the total proteinaceous matter, of which at least about 26 weight % is in a free form, relative to the total leucine,
  (iii) about 2 g of fat and about 6.2 to about 6.4 g of digestible carbohydrates,
for the prevention or treatment of a disease or condition which involves muscle decline in a mammal, wherein the nutritional composition is administered as 1 to 2 servings daily, each serving comprising about 150 kcal.

In another particular preferred embodiment, the nutritional composition comprises per 100 kcal:
  (ii) about 14 g of proteinaceous matter which comprises about 95 weight % of whey protein, relative to the total proteinaceous matter, and which comprises at least about 14 weight % of leucine, relative to the total proteinaceous matter, of which at least about 26 weight % is in a free form, relative to the total leucine,
  (iii) about 2 g of fat and about 6.2 g of digestible carbohydrates,
for use in the prevention or treatment of a disease or condition which involves muscle decline in a mammal, wherein the nutritional composition is administered as 1 to 2 servings daily, each serving comprising about 150 kcal.

Micronutrients

Elderly are at risk for micronutrient deficiencies, which is partly due to the fact that their energy intake is often reduced while many micronutrients recommendations increase [24]. As a result, 25-60% of the elderly does not meet the recommendations for micronutrient intake, and deficiencies of vitamins A, C, D, E, B6, folic acid, B12, calcium, magnesium, and zinc are commonly reported [25-27]. Moreover, micronutrients deficiencies are associated with frailty. Low intake of vitamin D, E, C and folate were associated with frailty [28], and low serum levels of carotenoids, vitamin E, vitamin D, selenium and zinc were observed in frail versus non-frail elderly [29].

Of the micronutrients, selenium, zinc, carotenoids, vitamin A, vitamin C and vitamin E all have antioxidant properties. Related to the published observation on the reversion by antioxidant supplementation of the decreased ability of leucine to stimulate muscle protein synthesis in elderly rats [30], a mixture of antioxidants is included in the nutritional composition.

Vitamin D3 is present in the composition for its demonstrated association with muscle strength and for the reduced incidence of falls and fractures in elderly with vitamin D supplementation; the minimum advised dose for reducing the risk of falls is between 700-1000 IU/day vitamin D (equivalent to 17.5 and 25 µg/day) [31-33]. This vitamin D dose is achieved with the proposed nutritional composition.

The B-vitamins folic acid, vitamin B6 and vitamin B12 are involved in the metabolic pathway of homocysteine, a known risk factor for common diseases in elderly [34], and are commonly deficient in elderly [27]. Because of the beneficial effect of folic acid, vitamin B6 and vitamin B12 on lowering blood homocysteine levels, these vitamins are present in the nutritional composition.

Hence, the nutritional composition according to the invention may optionally comprise one or more micronutrients, defined as minerals, trace elements and vitamins, selected from the group of sodium, potassium, chloride, calcium, phosphorous, magnesium, carotenoids, vitamin A, vitamin D3, vitamin E, vitamin K, vitamin B1, vitamin B2, vitamin B3, vitamin B5, vitamin B6, folic acid, vitamin B12, biotin, vitamin C, zinc, iron, copper, manganese, molybdenum, selenium, chromium, fluoride and iodide, preferably selected from the group of carotenoids, vitamin A, vitamin B6, vitamin B12, vitamin C, vitamin D3, vitamin E, folic acid, calcium, phosphorus, magnesium, selenium and zinc. Preferably, the nutritional composition according to the invention comprises carotenoids, vitamin A, vitamin D3, vitamin E, vitamin B6, vitamin C, folic acid, vitamin B12, selenium and zinc. Preferably, the nutritional composition according to the invention comprises per 100 kcal 10 to 500 µg of carotenoids, 80 to 140 µg of vitamin A, 8 to 750 µg of vitamin B6, 2 to 25 mg of vitamin C, 0.5 to 25 µg of vitamin D3, 0.5 to 10 mg of vitamin E, 10 to 150 kg of folic acid, 0.05 to 5 µg, in particular 0.07 to 5 µg of vitamin B12, 2.5 to 20 µg of selenium and 0.5 to 2.0 mg of zinc.

Medical Use

The nutritional composition according to the invention can advantageously be used for the prevention or treatment of a disease or condition involving muscle decline in a mammal, preferably a human of the age of 30 or more, more preferably of the age of 50 or more, most preferably in an elderly human. Muscle decline comprises any disease or condition selected from the group of sarcopenia; loss of muscle mass related to aging, during or following body weight maintenance, during or following energy restriction, during or following bed rest, during or following physical trauma treatment (such as fractures) or during or following weightlessness; insufficient muscle protein synthesis; muscle degradation; impaired muscle recovery; muscle damage; muscle proteolysis; muscle atrophy; muscle dystrophy; muscle catabolism; muscle wasting; loss of muscle strength; loss of muscle function; loss of physical capacity; loss of physical performance; impaired mobility; frailty; disability; and risk of falling.

Muscle recovery refers to the structural or functional repair of the muscle tissue (cells, fibers, sarcomers). Muscle damage is the mechanical disruption of muscle fiber, its membrane or the surrounding connective tissue or tendons. Muscle degradation refers to the breakdown or loss of quality of muscle tissue. Muscle atrophy refers to the wasting or loss of muscle tissue resulting from disease or lack of use. Muscular dystrophy is characterized by progressive muscle weakness and loss of muscle tissue. Muscle wasting is the loss of muscle tissue resulting from disease or lack of use. Physical capacity is the ability to perform physical activity. Physical performance is the ability to perform a physical task (e.g. balance, gait speed, strength or endurance) at a desired level. Frailty is a condition referring to a collection of symptoms or markers primarily due to the aging-related loss and dysfunction of skeletal muscle, such as: reduced physical activity, muscle weakness, decreased performance, physical weakness, poor endurance, exhaustion, slow walking speed, low muscle strength. In elderly, frailty will increase the risk of adverse events such as death, disability, and institutionalization. Disability refers to the inability to perform a physical activity.

According to a further embodiment, the nutritional composition according to the invention can advantageously be used for the dietary management of sarcopenia, the age-related loss of muscle mass, strength and function.

According to a further embodiment, the nutritional composition according to the invention can advantageously be used for any one of the following in a mammal, alone or in combination:
- support rebuilding muscle mass or muscle strength;
- manage sarcopenia;
- stimulate muscle protein synthesis, muscle strength, or muscle function;
- support improved muscle protein synthesis, muscle strength, or muscle function;
- improve or maintain mobility;
- meet the needs of a sarcopenic mammal;
- stimulate muscle protein synthesis;
- increase muscle mass or muscle strength;
- improve muscle strength or muscle function; and
- improve physical performance.

According to one embodiment, said mammal is a human of the age of 30 or more, more preferably of the age of 50 or more. More preferably, said mammal is an elderly human. In this respect, it is submitted that in the context of this application, an elderly human is a person of the age of 50 years or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

Dosage

The nutritional composition is administered as 1 to 2 servings daily, each serving comprising between 80 and 200 kcal, preferably about 150 kcal. Preferably, the nutritional composition is administered as one serving daily. Using a nutritional composition in a liquid form, the serving may comprise 50 to 250 ml of nutritional composition according to the invention, most preferably 200 ml per serving. Using a nutritional composition in a solid form, such as a powder, the serving may comprise 20 to 100 g of nutritional composition according to the invention, most preferably 30 to 70 g per serving, most preferably about 40 g per serving.

The nutritional composition may be administered in a dosage regime, which may vary in time and according to the patient's needs. A typical regime comprises the administration of 2 servings daily during the treatment period, e.g. for about 3 months, followed by the administration of one serving daily for prevention or as a maintenance dosage. Preferably, the nutritional composition is administered as one serving daily for prevention or as a maintenance dosage.

Nutritional Compositions

The present invention relates also to specific low-caloric high-protein nutritional compositions for stimulating muscle protein synthesis, either in liquid or in solid form.

According to one embodiment, the invention concerns a liquid nutritional composition, suitable for stimulating muscle protein synthesis, comprising per 100 ml:
(i) less than about 100 kcal of energy,
(ii) at least about 10 g of proteinaceous matter comprising at least about 80 weight % of whey protein, relative to the total proteinaceous matter, and which comprises at least about 11 weight % of leucine, relative to the total proteinaceous matter, of which at least about 20 weight % is in a free form, relative to the total leucine,
(iii) a source of fat and a source of digestible carbohydrates, and
(iv) one or more micronutrients selected from the group of carotenoids, vitamin A, calcium, magnesium, vitamin B6, vitamin C, vitamin D3, vitamin E, folic acid, vitamin B12, selenium and zinc.

Preferably, the liquid nutritional composition according to the invention comprises less than 90 kcal, preferably less than 80 kcal of energy per 100 ml.

According to a further embodiment, the invention concerns a liquid nutritional composition comprising per 100 ml:
(i) about 75 kcal of energy,
(ii) about 10.5 g of proteinaceous matter comprising about 10 g of whey protein, and comprising about 1.4 to about 1.5 g of leucine of which about 0.4 g is in a free form,
(iii) about 1.5 g of fat and about 4.4 to about 4.8 g of digestible carbohydrates,
(iv) about 0.15 mg carotenoids, about 75 µg vitamin A, about 375 µg vitamin B6, about 1.5 µg vitamin B12, about 16 mg vitamin C, about 10 µg vitamin D3, about 3.8 mg vitamin E, about 100 µg folic acid, about 7.5 µg selenium, about 1.1 mg zinc, and
(v) optionally, a source of dietary fibre.

According to a further embodiment, the invention concerns a liquid nutritional composition comprising per 100 ml:
(i) about 75 kcal of energy,
(ii) about 10.5 g of proteinaceous matter comprising about 10 g of whey protein, and comprising about 1.5 g of leucine of which about 0.4 g is in a free form,
(iii) about 1.5 g of fat and about 4.4 g of digestible carbohydrates,
(iv) about 0.15 mg carotenoids, about 75 µg vitamin A, about 375 µg vitamin B6, about 1.5 µg vitamin B12, about 16 mg vitamin C, about 10 µg vitamin D3, about 3.8 mg vitamin E, about 100 µg folic acid, about 7.5 µg selenium, about 1.1 mg zinc, and
(v) optionally, a source of dietary fibre.

According to a further embodiment, the invention concerns a liquid nutritional composition comprising per 100 ml:
(i) about 75 kcal of energy,
(ii) about 10.5 g of proteinaceous matter comprising about 10 g of whey protein, and comprising about 1.4 g of leucine of which about 0.4 g is in a free form,
(iii) about 1.5 g of fat and about 4.4 g of digestible carbohydrates,
(iv) about 0.15 mg carotenoids, about 75 µg vitamin A, about 375 µg vitamin B6, about 1.5 µg vitamin B12, about 16 mg vitamin C, about 10 µg vitamin D3, about 3.8 mg vitamin E, about 100 µg folic acid, about 7.5 µg selenium, about 1.1 mg zinc, and
(v) optionally, a source of dietary fibre.

When a source of dietary fibre is added to the above composition, it is preferable to add a total amount of about 0.83 g of dietary fiber per 100 ml comprising 0.63 g of GOS, 0.07 g of FOS/inulin and 0.14 g of low-viscosity pectin.

Said high amounts of whey protein can be achieved using inventive processes such as disclosed in WO 2009/113858, the contents of which are incorporated herein by reference.

According to one embodiment, the nutritional composition is packaged as a 100 to 300 ml serving, more preferably as a 200 ml serving.

According to one embodiment, the invention concerns a solid nutritional composition, suitable for stimulating muscle protein synthesis, comprising per 100 g of dry weight:
(i) less than 500 kcal of energy,
(ii) at least 49 g of proteinaceous matter comprising at least about 80 weight % of whey protein, relative to the total proteinaceous matter, and which comprises at least about 11 weight % of leucine, relative to the total proteinaceous matter, of which at least about 20 weight % is in a free form, relative to the total leucine,
(iii) a source of fat and a source of digestible carbohydrates,
(iv) one or more micronutrients selected from the group of carotenoids, vitamin A, calcium, magnesium, vitamin B6, vitamin C, vitamin D3, vitamin E, folic acid, vitamin B12, selenium and zinc.

The solid nutritional composition according to the invention comprises per 100 g, less than 445 kcal, preferably less than 395 kcal of energy.

According to one embodiment, the invention concerns a solid nutritional composition, suitable for stimulating muscle protein synthesis, comprising per 100 g of dry weight:
(i) about 375 kcal of energy,
(ii) about 52 to about 53 g of proteinaceous matter which comprises about 50 g of whey protein, and which comprises about 7.2 to about 7.5 g of leucine of which about 1.8 to about 2 g is in a free form,
(iii) about 7.5 g of fat and about 23 to about 24 g of digestible carbohydrates,
(iv) about 0.75 mg of carotenoids, about 376 kg of vitamin A, about 1.88 mg of vitamin B6, about 80 mg of vitamin C, about 50 kg of vitamin D3, about 18.8 mg of vitamin E, about 500 kg of folic acid, about 7.5 kg of vitamin B12, about 38 µg of selenium, about 5.5 mg of zinc, and
(v) optionally, a source of dietary fibre.

According to one embodiment, the invention concerns a solid nutritional composition, suitable for stimulating muscle protein synthesis, comprising per 100 g of dry weight:
(i) about 375 kcal of energy,
(ii) about 52 g of proteinaceous matter which comprises about 50 g of whey protein, and which comprises about 7.5 g of leucine of which about 1.9 g is in a free form,
(iii) about 7.5 g of fat and about 23 g of digestible carbohydrates,
(iv) about 0.75 mg of carotenoids, about 376 µg of vitamin A, about 1.88 mg of vitamin B6, about 80 mg of vitamin C, about 50 µg of vitamin D3, about 18.8 mg of vitamin E, about 500 µg of folic acid, about 7.5 µg of vitamin B12, about 38 kg of selenium, about 5.5 mg of zinc, and,
(v) optionally, a source of dietary fibre.

According to one embodiment, the invention concerns a solid nutritional composition, suitable for stimulating muscle protein synthesis, comprising per 100 g of dry weight:
(i) about 375 kcal of energy,
(ii) about 52 g of proteinaceous matter which comprises about 50 g of whey protein, and which comprises about 7.2 g of leucine of which about 2 g is in a free form,
(iii) about 7.5 g of fat and about 23 g of digestible carbohydrates,
(iv) about 0.75 mg of carotenoids, about 376 µg of vitamin A, about 1.88 mg of vitamin B6, about 80 mg of vitamin C, about 50 µg of vitamin D3, about 18.8 mg of vitamin E, about 500 µg of folic acid, about 7.5 µg of vitamin B12, about 38 µg of selenium, about 5.5 mg of zinc, and,
(v) optionally, a source of dietary fibre.

When a source of dietary fibre is added to the above composition, it is preferable to add a total amount of 4.13 g of dietary fiber comprising about 3.1 g of GOS, 0.34 g of FOS/inulin and 0.69 g of low-viscosity pectin per 100 g of dry weight.

Preferably, the solid nutritional composition according to the invention is formed as a powder, capable of being dissolved in an aqueous solution.

Preferably, the solid nutritional composition according to the invention is presented as a serving of about 20 to 70 g, more preferably of about 40 g.

The powder may be presented as a sachet, a cup, and the like, having the size of about the size of a serving, or it may be presented in a container, comprising several servings, such as 7 to 25 servings, e.g. 10 to 25 servings, optionally accompanied by a metering device such as a spoon.

With regard to both the liquid and solid nutritional composition according to the invention, one or more of the following specifications apply:
- the amount of fat may vary between 10 and 35 en %, preferably between 15 and 30 en %;
- the amount of carbohydrate may vary between 10 and 35 en %, preferably between 15 and 30 en %;
- the relative amounts of the sum of fat and carbohydrate range between 10 and 60 en %, e.g. between 30 and 60 en %;
- the proteinaceous matter comprises at least about 85 weight % of whey protein, preferably at least about 90 weight %, and more preferably about 95 weight % of whey protein.
- the proteinaceous matter comprises at least 45 weight %, preferably at least 47 weight %, and more preferably at least about 50 weight % of essential amino acids (EAA).
- the proteinaceous matter comprises at least about 12 weight %, preferably at least about 12.5 weight %, more preferably at least about 13 weight % of leucine.
- the proteinaceous matter comprises at least about 22.5 weight %, preferably at least about 26 weight % of leucine in a free form, relative to the total amount of leucine.
- the proteinaceous matter comprises total leucine, total valine and total isoleucine in a total leucine:valine:isoleucine ratio of about 1.7-3:1:1.
- the nutritional composition further comprises one or more dietary fibres selected from the group of short chain GOS, long chain FOS, inulin and low-viscosity pectin.

The compositions according to the invention may be prepared by the methods known to the skilled person, in particular as disclosed in WO 2009/113858, which is incorporated herein by reference in its entirety. Powders can be made by methods commonly known in the art by the skilled person, such as spray drying the liquid composition or dry-mixing of powder ingredients, or a combination of both.

The invention will now be further elucidated by several examples, without being limited or bound thereby.

EXPERIMENTAL

1. Clinical Study

Figure 1:
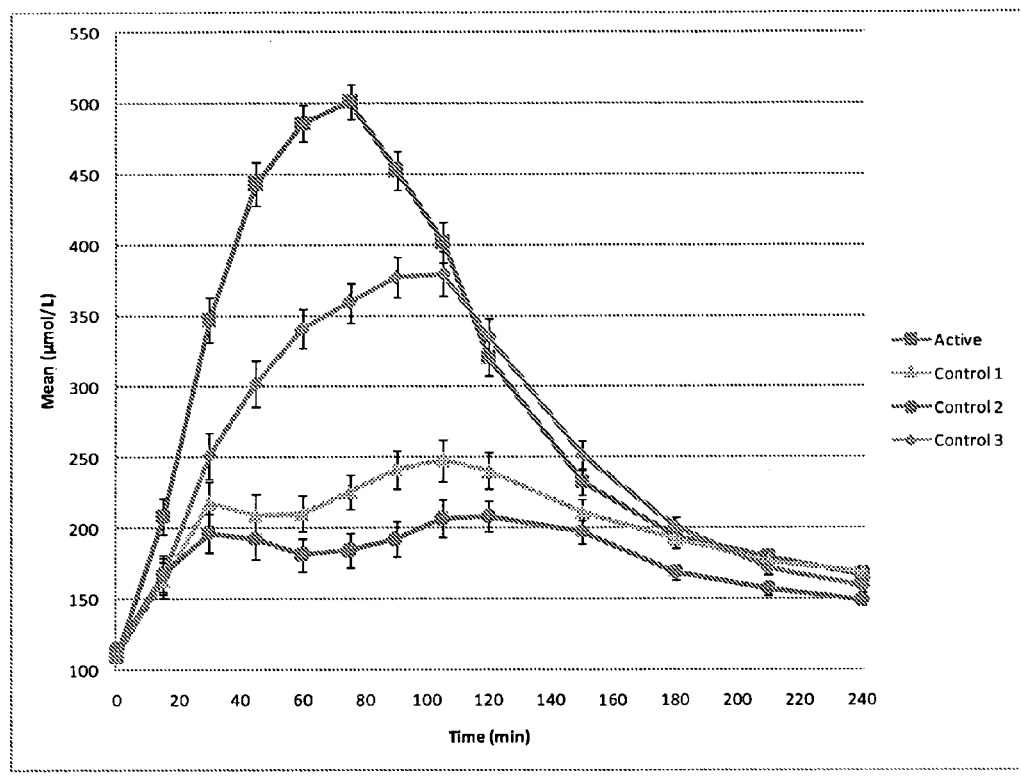
FIG. 1: Time curves for mean serum leucine concentrations

A clinical study was performed aimed to evaluate the acute effect of protein source and caloric density of high protein oral nutritional composition on serum amino acid levels in elderly. For this, a high whey-protein (21 g), leucine-rich (3 g), low-caloric composition (composition according to the invention—Active) was compared with an iso-nitrogeneous oral nutritional composition with casein-protein (Control 1, low-caloric) or with high caloric density (Control 2, casein-protein; Control 3, whey-protein). A randomised, controlled, single blind, cross-over design in 12 healthy elderly subjects (5 male, 7 female), recruited from a volunteer database at a clinical research unit in the Netherlands was used. Subjects were between 65 and 70 years of age and had normal weight or slight overweight (Body Mass Index (BMI) range 21.7-29.7 kg/m2). Statistics were performed using a mixed model analysis of variance with random effect for subjects, fixed effect for protein source (2 levels: whey, casein) and caloric density (2 levels: low, high), and fixed interaction of protein source*caloric density. The statistical model included serum albumin, serum C-reactive protein (CRP), and baseline serum outcome parameter concentration as covariates. Additional analyses on maximum serum leucine concentration ($Leu_{max}$) were performed, using age, physical activity level, sex, or BMI (categories 25 and >25 kg/m2) as additional covariate. We used 2-sided tests with α=0.05.

$Leu_{max}$ was significantly higher for Active compared to Control 1 (521 vs. 260 μmol/L, p<0.001).

The effect of protein source was similar for the high-caloric products; $Leu_{max}$ was significantly higher for Control 3 compared to Control 2 (406 vs. 228 μmol/L, p<0.001). Intake of the low-caloric products led to significantly higher $Leu_{max}$ compared to the high-caloric products (p<0.001 for pooled analyses). The effect of protein source was stronger for the low-caloric products (p<0.001 for interaction effect). These effects (of protein source, caloric density, and interaction) were also shown for maximum total serum essential amino acid concentration ($EAA_{max}$) and maximum total serum amino acid concentration ($AA_{max}$). Protein source and caloric density also affected incremental area under the curve (iAUC) during 4 hours after product intake for leucine (44,588 μmol/L*min [Active] vs. 22,207 μmol/L*min [Control 1], p<0.001; 35,952 μmol/L*min [Control 3] vs. 15,793 μmol/L*min [Control 2], p<0.001; and p<0.001 for pooled analyses of low-caloric vs. high-caloric products). The same effects were shown for iAUC EAA, and iAUC AA. Time necessary to reach half the iAUC (t %) for leucine was significantly shorter for Active compared to Control 1 (87 vs. 119 min, p<0.001), and was significantly shorter for Control 3 compared to Control 2 (101 vs. 118 min, p=0.003). The effect of protein source on t % was also found for EAA and AA. Maximum serum insulin concentration did neither differ between Active and Control 1 (p=0.915), nor between Control 3 and Control 2 (p=0.989). There was no interaction effect between protein source and caloric density for maximum serum insulin concentration (p=0.933). The absence of effect of protein source and interaction effect was also found for serum insulin iAUC. Maximum serum glucose concentration was significantly lower for Active compared to Control 1: 5.54 vs. 6.05 mmol/L (p=0.013). The effect of protein source was absent for the high-caloric products (Control 3 [6.42 mmol/L] vs. Control 2 [6.66 mmol/L], p=0.195). There was no interaction effect between protein source and caloric density for maximum serum glucose concentration (p=0.314). Effect of protein source and interaction effect were absent for serum glucose iAUC. The effect of caloric density was shown for maximum concentration and iAUC, both for insulin and glucose, with lower values for the low-caloric products (all p-values<0.001 for pooled analyses). There were no clinically relevant differences in adverse events and GI symptoms observed. Vital signs and serum valine and isoleucine profiles do not lead to safety concerns. Active was associated with less satiety than Control 1; especially hunger was larger, over 4 hours after intake.

This study confirmed that whey protein is a faster source of amino acids than casein protein, resulting in higher levels of serum amino acids. Surprisingly, low-caloric density further supports the effect of protein source on levels of amino acids. The combination of whey protein and low-caloric density gave the most pronounced effect on maximum leucine concentration. Therefore, the Active product is preferred to provoke muscle protein synthesis; at least over casein products and probably also over a high-caloric equivalent. No clinically relevant differences in insulin and glucose levels were observed between the whey and casein containing products. There were no safety concerns related to the consumption of 1 dosage of any of the study products. The clinical study showed that the composition (150 kcal in the clinical study) resulted in higher blood levels (maximum/peak level and iAUC) of leucine, essential amino acids and total amino acids compared with a similar proteinaceous composition in 320 kcal (about 26en % protein). The composition results in higher and faster blood levels (maximum/peak level and iAUC) of leucine, essential amino acids and total amino acids compared with a proteinaceous composition containing 100% slow/casein protein, either as 150 kcal or 320 kcal.

These data suggests that the (peripheral) bioavailability of anabolic amino acids (leucine and essential amino acids) is optimal with a composition comprising whey-leucine as the protein source in a formulation containing low calories (party originating from fat and CHO). Since it is known from literature that blood leucine and essential amino acid levels are positively related to stimulation of protein synthesis in the muscle, it is anticipated that stimulation of muscle protein synthesis is optimal with the proposed nutritional composition.

Details

Subjects and Methods

Subjects 12 healthy elderly subjects (5 male, 7 female; age between 65 and 70 years BMI range 21.7-29.7 kg/m²) participated in this randomized, controlled, single blind, cross-over study.

Subjects with known or suspected Diabetes Mellitus (glucose concentration ≥7.0 mmol/L) were excluded from the study. Moreover, subjects were excluded in case of any (history of) gastrointestinal disease that interferes with gastrointestinal function, known allergy to milk and milk products or galactosaemia, current or recent (within past three months) smoking, current infection or fever in the last 7 days at the discretion of the physician, use of antibiotics within 3 weeks of study entry, current use of corticosteroids, hormones, antacids or any medication influencing gastric acid production, requirement for any nutritional support or adherence to any specific diet (e.g. weight loss, vegetarian).

All subjects signed for informed consent and were randomly allocated to receive a unique order of the 4 study products. The study products were: 1) The product according to the invention: Active: high whey-leucine, 150 kcal; 2) Control 1: high casein, 150 kcal; 3) Control 2: high casein, 320 kcal; 4) Control 3: high whey-leucine, 320 kcal (Table 1). Each study product was given as a bolus (consumed within 5 minutes) in a liquid formulation.

TABLE 1

Nutritional composition of the study products

| Nutrients | Unit | Active High-whey/Leu 150 kcal | Control 1 High casein 150 kcal | Control 2 High casein 320 kcal | Control 3 High whey/Leu 320 kcal |
|---|---|---|---|---|---|
| Energy | kcal | 150 | 150 | 320 | 320 |
| Protein | g | 21 | 21 | 21 | 21 |
| intact whey | g | 20 | — | — | 20 |
| casein | g | — | 21 | 21 | — |
| Leucine (total) | g | 3 | 2 | 2 | 3 |
| EAA (total) | g | 10 | 9 | 9 | 10 |
| Carbohydrate | g | 10.5 | 10.1 | 32.0 | 32.9 |
| Fat | g | 3 | 3 | 12 | 12 |

Experimental Protocol

Figure 4:
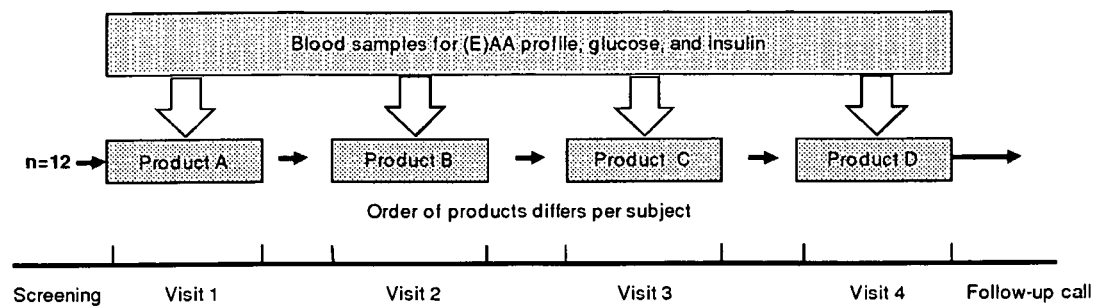
FIG. 4: Schematic diagram of clinical study

Subjects visited the research location in a fasting state on 4 separate mornings. After taking the study product, subjects stayed at the location for 4 hours to undergo study assessments. Visits were at least 1 week apart (7-10 days after the preceding visit). FIG. 4 shows a schematic diagram of the study.

On each visit, subjects were asked about intercurrent illnesses, intercurrent use of medication and nutritional supplements, and their dietary intake and physical activities during the last 24 hours. If subjects a) experienced an infection or fever during the last 7 days, b) used antibiotics, corticosteroids, hormones, antacids, or any medication influencing gastric acid production, or c) were not in a fasting state, the visit was rescheduled.

The protocol at each visit was identical and included: GI tolerance was assessed at baseline (−30 min), blood pressure (BP) and heart rate (HR) at t=−20 min. A flexible canula for blood drawing was placed in a vein of the forearm for blood sampling. The study product was consumed (T0) and blood samples (5 ml) were taken throughout the 4-hour study period: 2 samples at t=−15 min and the other 13 samples at t=: 0 min (before product intake), 15 min, 30 min, 45 min, 1 h, 1 h 15 min, 1 h 30 min, 1 h 45 min, 2 h, 2 h 30 min, 3 h, 3 h 30 min, and 4 h. Blood samples were taken with the subject in sitting position. Blood pressure, heart rate and GI tolerance were measured again at t=4 h.

Sample Analysis

Blood was centrifuged to obtain serum, which was subsequently stored at −20 degrees Celsius until analysis. Serum concentrations of 21 amino acids (leucine, isoleucine, valine, histidine, lysine, methionine, phenylalanine, threonine, tryptophan, alanine, arginine, asparagines, aspartic acid, citrulline, cysteine, glutamic acid, glutamine, glycine, serine, taurine, and tyrosine) were analysed for all timepoints, using HPLC, as is well known to the skilled person. The concentrations of the 9 essential amino acids: histidine, isoleucine, leucine, lysine, methionine, phenylalanine, threonine, tryptophan, and valine are summed (EAA). The concentrations of all 21 amino acids are summed (AA).

Statistical Analysis

All dependent variables were analysed using a mixed model with a random effect for subjects, a fixed effect for the factors protein (2 levels: whey, casein) and caloric density (2 levels: low, high), and a fixed interaction of protein*caloric density. In separate analyses, to analyse differences between treatments, the difference between the Active product and the Control 1 was analysed, as well as Active vs. Control 3 and Control 1 vs. Control 2.

Results

Serum Leucine

Time curves for mean serum leucine concentration are shown in FIG. 1.

Maximum serum leucine concentration was significantly higher in Active than in Control 1: 521 vs. 260 µmol/L (p<0.001). This difference between whey+leucine vs. casein for the low-caloric products was, to a lesser extent, also seen for the high-caloric products (Control 3 [406 µmol/L] vs. Control 2 [228 µmol/L], p<0.001).

Pooled analysis of the low-caloric vs. the high-caloric products (Active and Control 1 vs. Control 2 and Control 3) showed significantly higher $Leu_{max}$ for the low-caloric density (p<0.001). This effect was stronger for the high whey-protein, leucine-rich products (Active vs. Control 3, p<0.001), than for the high casein-protein products (Control 1 and Control 2, p=0.042), reflected by the significant interaction effect between protein source and caloric density (p<0.001).

iAUC Leu was significantly higher in Active than in Control 1: 44588 vs. 22207 µmol/L*min (p<0.001). This difference between whey+leucine vs. casein for the low-caloric products was also seen for the high-caloric products (Control 3 [35952 µmol/L*min] vs. Control 2 [15793 µmol/L*min], p<0.001). Pooled analysis of the low-caloric vs. the high-caloric products showed significantly higher iAUC Leu for the low-caloric density (p<0.001). There was no significant interaction effect between protein source and caloric density for iAUC Leu (p=0.286).

$t_{1/2}$ Leu was significantly lower in Active than in Control 1: 87 vs. 119 min (p<0.001). A difference between whey+leucine vs. casein was also seen for the high-caloric products (Control 3 [101 min] vs. Control 2 [118 min], p=0.003). There was no significant difference between low and high caloric density (p=0.100). There was a tendency for an interaction effect between protein source and caloric density (p=0.074).

Serum Essential Amino Acids (EAA)

Figure 2:
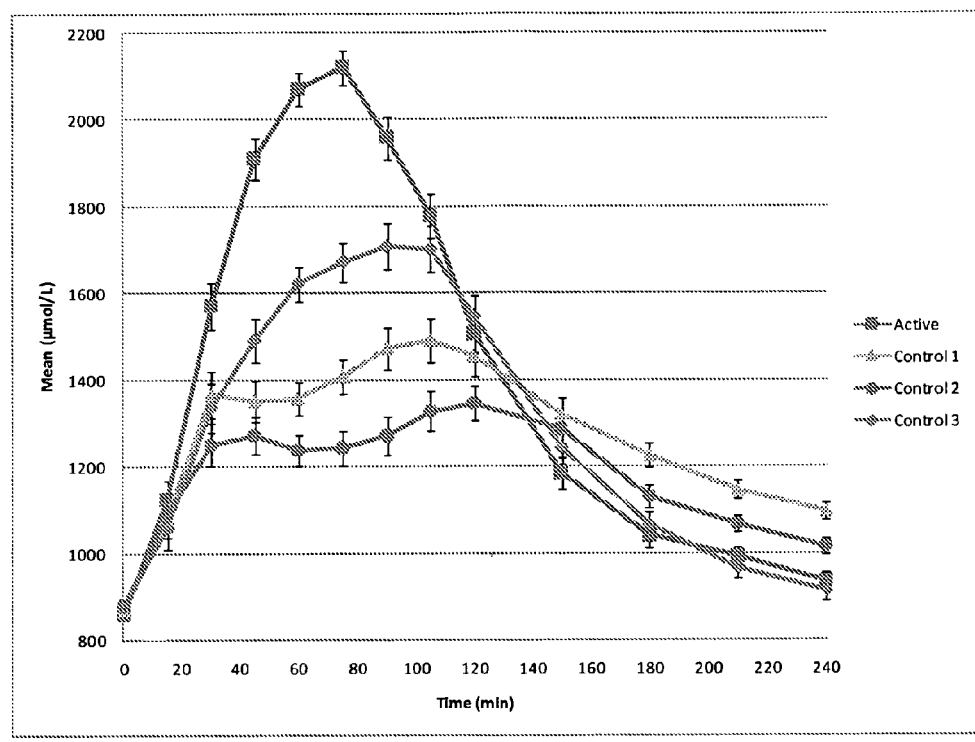
FIG. 2: Time curves for mean total serum essential amino acid concentrations

Time curves for mean total serum essential amino acid concentration are shown in FIG. 2. Total serum essential amino acid concentration at baseline ($EAA_{baseline}$) was at similar level for all products (860-890 µmol/L). $EAA_{baseline}$ was included as covariate in the statistical model. Maximum serum essential amino acid concentration ($EAA_{max}$) was significantly higher in Active than in Control 1: 2187 vs. 1540 µmol/L (p<0.001). This difference between whey+leucine vs. casein for the low-caloric products was, to a lesser extent, also seen for the high-caloric products (Control 3 [1792 µmol/L] vs. Control 2 [1420 µmol/L], p<0.001).

Pooled analysis of the low-caloric vs. the high-caloric products showed significantly higher $EAA_{max}$ for the low-caloric density (p<0.001). This effect was stronger for the high whey-protein, leucine-rich products (Active vs. Control 3, p<0.001), than for the high casein-protein products (Control 1 and Control 2, p=0.023), reflected by the significant interaction effect between protein source and caloric density (p<0.001).

iAUC EAA was significantly higher in Active than in Control 1: 129793 vs. 100516 µmol/L*min (p<0.001). This difference between whey+leucine vs. casein for the low-caloric products was also seen for the high-caloric products (Control 3 [101181 µmol/L*min] vs. Control 2 [75181 µmol/L*min], p<0.001). Pooled analysis of the low-caloric vs. the high-caloric products showed significantly higher iAUC EAA for the low-caloric density (p<0.001). There was no significant interaction effect between protein source and caloric density for iAUC EAA (p=0.673).

$t_{1/2}$ EAA was significantly lower in Active than in Control 1: 83 vs. 115 min (p<0.001). A difference between whey+ leucine vs. casein was also seen for the high-caloric products (Control 3 [94 min] vs. Control 2 [117 min], p<0.001). There was a tendency for an effect of caloric density on $t_h$ EAA (p=0.093). Interaction effect between protein source and caloric density was absent (p=0.223).

Total Amino Acids (AA)

Figure 3:
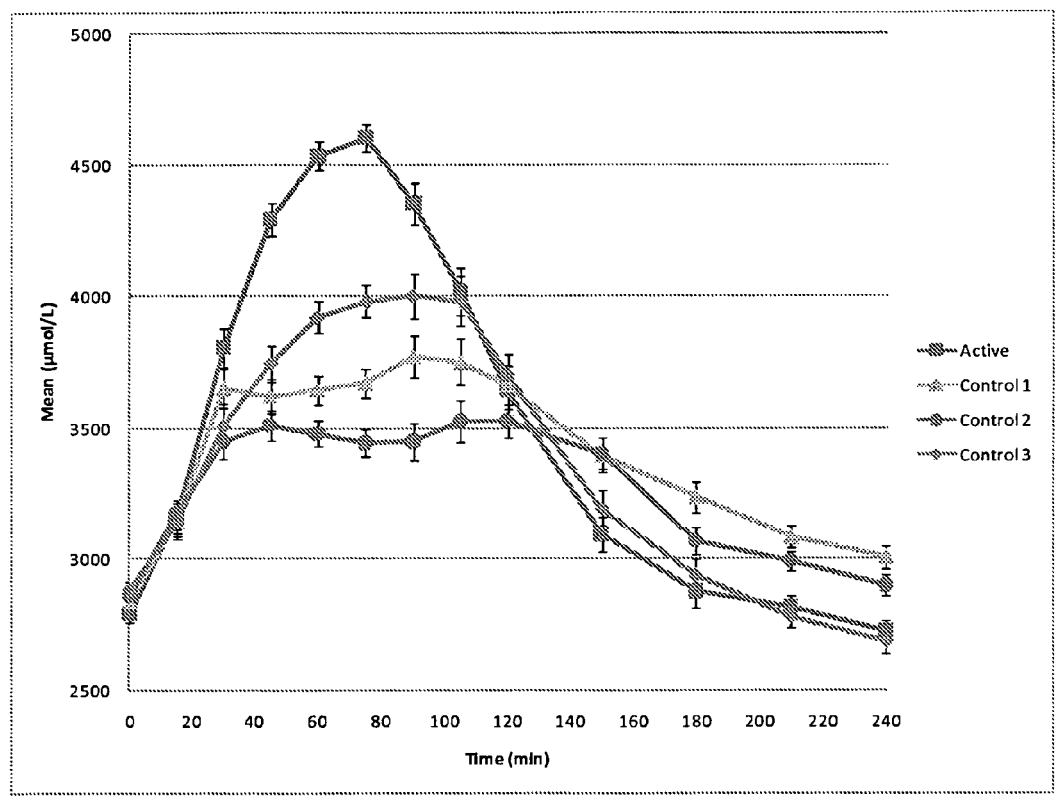
FIG. 3: Time curves for mean total serum amino acid concentration

Time curves for mean total serum amino acid concentration are shown in FIG. 3. Total serum amino acid concentration at baseline ($AA_{baseline}$) was similar for all products (2780-2880 µmol/L). $AA_{baseline}$ was included as covariate in the statistical model.

Maximum serum amino acid concentration ($AA_{max}$) was significantly higher in Active than in Control 1: 4687 vs. 3946 µmol/L (p<0.001). This difference between whey+leucine vs. casein for the low-caloric products was also seen for the high-caloric products (Control 3 [4141 µmol/L] vs. Control 2 [3699 µmol/L], p<0.001).

Pooled analysis of the low-caloric vs. the high-caloric products showed significantly higher $AA_{max}$ for the low-caloric density (p<0.001). This effect was stronger for the high whey-protein, leucine-rich products (Active vs. Control 3, p<0.001), than for the high casein-protein products (Control 1 and Control 2, p=0.003), reflected by the significant interaction effect between protein source and caloric density (p=0.015).

iAUC AA was significantly higher in Active than in Control 1: 162702 vs. 143018 µmol/L*min (p=0.032). This difference between whey+leucine vs. casein for the low-caloric products was also seen for the high-caloric products (Control 3 [128047 µmol/L*min] vs. Control 2 [105525 µmol/L*min], p=0.008). Pooled analysis of the low-caloric vs. the high-caloric products showed significantly higher iAUC AA for the low-caloric density (p<0.001). There was no significant interaction effect between protein source and caloric density for iAUC AA (p=0.819).

$t_{1/2}$ AA was significantly lower in Active than in Control 1: 78 vs. 101 min (p<0.001). A difference between whey+leucine vs. casein was also seen for the high-caloric products (Control 3 [87 min] vs. Control 2 [103 min], p=0.007). There was no significant difference between low and high caloric density (p=0.199). Interaction effect between protein source and caloric density for $t_{1/2}$ AA was absent (p=0.413).

CONCLUSION

Serum leucine concentration increased to above 500 µmol/L after intake of the high whey-protein, leucine-rich, low-caloric product. The difference in $Leu_{max}$ with the high casein-protein, low-caloric product (520 vs. 260 µmol/L) was higher than expected. The a priori assumption on the effect of intervention was a 1001 µmol/L difference in $Leu_{max}$ between Active and Control 1, estimated from Dangin et al. [15]. Serum EAA concentrations were also higher after intake of the high whey-protein, leucine-rich, low-caloric product compared with the high casein-protein, low-caloric product.

This study confirmed that whey protein is a faster source of amino acids than casein protein, which is considered a slow protein [7]. The rate of appearance of amino acids in the circulation was much higher, reflected by the time to half the iAUC. $t_{1/2}$ was shorter for the high whey-protein, leucine-rich products; not only for leucine and total essential amino acids, but also for total amino acids. Time curves for individual amino acids, other than leucine, confirmed this. The high leucine peak seen for the high whey-protein, leucine-rich products was more pronounced for the low-caloric product. $Leu_{max}$ values for the high-caloric products were 406 (high whey-protein, leucine-rich) and 228 (high casein-protein) µmol/L. Leucine concentrations above 300 µmol/L seemed effective in stimulating muscle protein synthesis in elderly [35] [amino acid infusion]; [36] [leucine supplemented nutrition]). Although no clear data exist on the dose—response relation between serum leucine and muscle protein synthesis, we hypothesize that the low-caloric high whey-protein, leucine-rich product is the preferred product for stimulating muscle protein synthesis.

2. Nutritional Compositions

The following nutritional compositions according to the invention are suitable for the prevention or treatment of a disease or condition in a mammal, for instance an elderly mammal, which involves muscle protein synthesis.

| Ingredient | Most preferred Per 100 kcal | Liquid sip-feed I (per 100 ml) | Liquid sip-feed II (per 100 ml) | Liquid sip-feed III (per 100 ml) | Powder I (per 100 g) | Powder II (per 100 g) | Powder III (per 100 g) |
|---|---|---|---|---|---|---|---|
| Energy (kcal) | 100 | 75 | 75 | 75 | 375 | 375 | 375 |
| protein (En %) | 55 | 56 | 55 | 55 | 56 | 55 | 55 |
| fat (En %) | 18 | 18 | 18 | 18 | 18 | 18 | 18 |
| dig. carbs (En %) | 25 | 23 | 24 | 24 | 23 | 25 | 25 |
| indig. carbs (En %) | 2 | 3 | 3 | 3 | 3 | 2 | 2 |
| Total protein (g) | 14.0 | 10.5 | 10.5 | 10.5 | 52.7 | 51.9 | 51.9 |
| Intact whey prot (g) (wt % of p.m.) | 13.3 (95 wt %) | 10.0 (95 wt %) | 10 (95 wt %) | 10 (95 wt %) | 50.0 (95 wt %) | 49.1 (95 wt %) | 49.1 (95 wt %) |
| Free leucine (g) (wt % of total Leu) | 0.5 (26 wt %) | 0.4 (26 wt %) | 0.4 (26 wt %) | 0.4 (26 wt %) | 2.0 (26 wt %) | 1.8 (26 wt %) | 1.9 (26 wt %) |

-continued

| Ingredient | Most preferred Per 100 kcal | Liquid sip-feed I (per 100 ml) | Liquid sip-feed II (per 100 ml) | Liquid sip-feed III (per 100 ml) | Powder I (per 100 g) | Powder II (per 100 g) | Powder III (per 100 g) |
|---|---|---|---|---|---|---|---|
| Total leucine (g) (wt % of p.m.) | 2.0 (14 wt %) | 1.5 (14 wt %) | 1.4 (14 wt %) | 1.5 (14 wt %) | 7.5 (14 wt %) | 7.2 (14 wt %) | 7.5 (14 wt %) |
| Total isoleucine (g) | 1.0 | 0.75 | 0.7 | 0.7 | 3.75 | 3.5 | 3.5 |
| Total valine (g) | 1.0 | 0.75 | 0.7 | 0.7 | 3.75 | 3.5 | 3.5 |
| EAA (g) (wt % of p.m.) | 7.0 (50 wt %) | 5.3 (50 wt %) | 5.3 (50 wt %) | 5.3 (50 wt %) | 26.4 (50 wt %) | 26 (50 wt %) | 26 (50 wt %) |
| Fat (g) | 2.0 | 1.5 | 1.5 | 1.5 | 7.5 | 7.5 | 7.5 |
| Digestible carbs (g) | 6.4 | 4.8 | 4.4 | 4.4 | 23.9 | 23.1 | 23.1 |
| Indigestible carbs (g) | 1.11 | 0.84 | 0.98 | 0.98 | 4.17 | 4.17 | 4.17 |
| GOS (g) | 0.83 | 0.63 | 0.63 | 0.63 | 3.13 | 3.13 | 3.13 |
| FOS/inulin (g) | 0.09 | 0.07 | 0.07 | 0.07 | 0.35 | 0.35 | 0.35 |
| Low-visc. pectin (g) | 0.19 | 0.14 | 0.14 | 0.14 | 0.69 | 0.69 | 0.69 |
| Zinc (mg) | 1.5 | 1.1 | 1.1 | 1.1 | 5.5 | 5.5 | 5.5 |
| Selenium (µg) | 10 | 7.5 | 7.5 | 7.5 | 37.5 | 38 | 38 |
| Carotenoids (µg) | 200 | 150 | 150 | 150 | 750 | 750 | 750 |
| Vitamin C (mg) | 21.3 | 16.0 | 16.0 | 16.0 | 80.0 | 80.0 | 80.0 |
| Vitamin E (mg-α-TE) | 5.0 | 3.8 | 3.8 | 3.8 | 18.8 | 19 | 19 |
| Vitamin D3 (µg) | 13.3 | 10.0 | 10.0 | 10.0 | 50.0 | 50.0 | 50.0 |
| Vitamin B6 (µg) | 500 | 375 | 375 | 375 | 1875 | 1882 | 1882 |
| Folic acid (µg) | 133 | 100 | 100 | 100 | 500 | 501 | 501 |
| Vitamin B12 (µg) | 2.0 | 1.5 | 1.5 | 1.5 | 7.5 | 7.5 | 7.5 |
| Vitamin A (µg) | 100 | 75 | 75 | 75 | 375 | 376 | 376 |
| Serving size | — | 200 ml | 200 ml | 200 ml | 40 g | 40 g | 40 g |

REFERENCES

1. Rolland, Y., et al., *Sarcopenia: its assessment, etiology, pathogenesis, consequences and future perspectives.* J Nutr Health Aging, 2008. 12(7): p. 433-50.
2. Short, K. R. and K. S. Nair, *Mechanisms of sarcopenia of aging.* J Endocrinol Invest, 1999. 22(5 Suppl): p. 95-105.
3. Boirie, Y., *Physiopathological mechanism of sarcopenia.* J Nutr Health Aging, 2009. 13(8): p. 717-23.
4. Guillet, C., et al., *Impaired anabolic response of muscle protein synthesis is associated with S6K1 dysregulation in elderly humans.* Faseb J, 2004. 18(13): p. 1586-7.
5. Rasmussen, B. B., et al., *Insulin resistance of muscle protein metabolism in aging.* Faseb J, 2006. 20(6): p. 768-9.
6. Cuthbertson, D., et al., *Anabolic signaling deficits underlie amino acid resistance of wasting, aging muscle.* Faseb 1, 2005. 19(3): p. 422-4.
7. Boirie, Y., et al., *Slow and fast dietary proteins differently modulate postprandial protein accretion.* Proc Natl Acad Sci USA, 1997. 94(26): p. 14930-5.
8. Katsanos, C. S., et al., *A high proportion of leucine is required for optimal stimulation of the rate of muscle protein synthesis by essential amino acids in the elderly.* Am J Physiol Endocrinol Metab, 2006. 291(2): p. E381-7.
9. Volpi, E., et al., *Essential amino acids are primarily responsible for the amino acid stimulation of muscle protein anabolism in healthy elderly adults.* Am J Clin Nutr, 2003. 78(2): p. 250-8.
10. Paddon-Jones, D., et al., *Differential stimulation of muscle protein synthesis in elderly humans following isocaloric ingestion of amino acids or whey protein.* Exp Gerontol, 2006. 41(2): p. 215-9.
11. Katsanos, C. S., et al., *Aging is associated with diminished accretion of muscle proteins after the ingestion of a small bolus of essential amino acids.* Am J Clin Nutr, 2005. 82(5): p. 1065-73.
12. Paddon-Jones, D., et al., *Amino acid ingestion improves muscle protein synthesis in the young and elderly.* Am J Physiol Endocrinol Metab, 2004. 286(3): p. E321-8.
13. Anthony, J. C., et al., *Leucine stimulates translation initiation in skeletal muscle of postabsorptive rats via a rapamycin-sensitive pathway.* J Nutr, 2000. 130(10): p. 2413-9.
14. Rieu, I., et al., *Increased availability of leucine with leucine-rich whey proteins improves postprandial muscle protein synthesis in aging rats.* Nutrition, 2007. 23(4): p. 323-31.
15. Dangin, M., et al., *The rate of protein digestion affects protein gain differently during aging in humans.* J Physiol, 2003. 549(Pt 2): p. 635-44.
16. Bohe, J., et al., *Human muscle protein synthesis is modulated by extracellular, not intramuscular amino acid availability: a dose-response study.* J Physiol, 2003. 552(Pt 1): p. 315-24.
17. Wolfe, R. R., *Protein supplements and exercise.* Am J Clin Nutr, 2000. 72(2 Suppl): p. 5515-75.
18. Marieb, E. N., *Human anatomy & Physiology.* 4 ed. 1998, Menlo Park, Calif.: Benjamin/Cummings Science Publishing. 1192.
19. Dangin, M., et al., *Influence of the protein digestion rate on protein turnover in young and elderly subjects.* J Nutr, 2002. 132(10): p. 32285-335.
20. Dangin, M., et al., *The digestion rate of protein is an independent regulating factor of postprandial protein retention.* Am J Physiol Endocrinol Metab, 2001. 280(2): p. E340-8.
21. Boirie, Y., P. Gachon, and B. Beaufrere, *Splanchnic and whole-body leucine kinetics in young and elderly men.* Am J Clin Nutr, 1997. 65(2): p. 489-95.
22. Volpi, E., et al., *Oral amino acids stimulate muscle protein anabolism in the elderly despite higher first-pass splanchnic extraction.* Am J Physiol, 1999. 277(3 Pt 1): p. E513-20.
23. Clarkston, W. K., et al., *Evidence for the anorexia of aging: gastrointestinal transit and hunger in healthy elderly vs. young adults.* Am J Physiol, 1997. 272(1 Pt 2): p. R243-8.
24. WHO, *Keep fit for life: meeting the nutritional needs of older persons.* 2002.

25. Holick, M. F., *Vitamin D deficiency*. N Engl J Med, 2007. 357(3): p. 266-81.
26. Lesser, S., et al., *Nutritional situation of the elderly in Eastern/Baltic and Central/Western Europe—the Ageing Nutrition project*. Ann Nutr Metab, 2008. 52 Suppl 1: p. 62-71.
27. Raats, M. L., L. de Groot, and W. van Staveren, *Food for the ageing population*. 2009, Cambridge, England: Woodhead Publishing Limited.
28. Bartali, B., et al., *Low nutrient intake is an essential component of frailty in older persons*. J Gerontol A Biol Sci Med Sci, 2006. 61(6): p. 589-93.
29. Semba, R. D., et al., *Low serum micronutrient concentrations predict frailty among older women living in the community*. J Gerontol A Biol Sci Med Sci, 2006. 61(6): p. 594-9.
30. Marzani, B., et al., *Antioxidant supplementation restores defective leucine stimulation of protein synthesis in skeletal muscle from old rats*. J Nutr, 2008. 138(11): p. 2205-11.
31. Bischoff-Ferrari, H. A., et al., *Higher 25-hydroxyvitamin D concentrations are associated with better lower-extremity function in both active and inactive persons aged> or =60 y*. Am J Clin Nutr, 2004. 80(3): p. 752-8.
32. Bischoff-Ferrari, H. A., et al., *Prevention of nonvertebral fractures with oral vitamin D and dose dependency: a meta-analysis of randomized controlled trials*. Arch Intern Med, 2009. 169(6): p. 551-61.
33. Bischoff-Ferrari, H. A., et al., *Fall prevention with supplemental and active forms of vitamin D: a meta-analysis of randomised controlled trials*. Bmj, 2009. 339: p. b3692.
34. Seshadri, S., et al., *Plasma homocysteine as a risk factor for dementia and Alzheimer's disease*. N Engl 1 Med, 2002. 346(7): p. 476-83.
35. Volpi, E., et al., *Exogenous amino acids stimulate net muscle protein synthesis in the elderly*. J Clin Invest, 1998. 101(9): p. 2000-7.
36. Rieu, I., et al., *Leucine supplementation improves muscle protein synthesis in elderly men independently of hyperaminoacidaemia*. J Physiol, 2006. 575(Pt 1): p. 305-15.

The invention claimed is:

1. A nutritional composition comprising per 100 kcal:
   (i) at least about 12 g of proteinaceous matter which comprises at least about 80 weight % of whey protein, relative to the total proteinaceous matter, and which comprises at least about 11 weight % of leucine, relative to the total proteinaceous matter, of which at least about 20 weight % is in a free form, relative to the total leucine,
   (ii) a source of fat and a source of digestible carbohydrates,
for use in the prevention or treatment of a disease or condition which involves muscle decline in a mammal, wherein the nutritional composition is administered as 1 to 2 servings daily, each serving comprising between 80 and 200 kcal.

2. The nutritional composition according to claim 1, wherein the proteinaceous matter comprises at least about 12.5 g of proteinaceous matter per 100 kcal.

3. The nutritional composition according to claim 1, wherein the proteinaceous matter comprises at least about 45 weight % of essential amino acids (EAA).

4. The nutritional composition according to claim 1, wherein the proteinaceous matter comprises at least about 12 weight % of leucine.

5. The nutritional composition according to claim 1, wherein the total leucine comprises at least about 22.5 weight % of leucine in a free form, relative to the total amount of leucine.

6. The nutritional composition according to claim 1, wherein the proteinaceous matter comprises a total amount of leucine, valine and isoleucine in a leucine:valine:isoleucine ratio of about 1.7-3:1:1.

7. The nutritional composition according to claim 1, wherein the nutritional composition further comprises one or more dietary fibers selected from the group of short chain GOS, long chain FOS, inulin and low-viscosity pectin.

8. The nutritional composition according to claim 1, wherein the nutritional composition further comprises carotenoids, vitamin A, vitamin B6, vitamin C, vitamin D3, vitamin E, folic acid, vitamin B12, selenium and zinc.

9. A nutritional composition comprising per 100 kcal:
   (ii) about 14 g of proteinaceous matter which comprises about 95 weight % of whey protein, relative to the total proteinaceous matter, and which comprises at least about 14 weight % of leucine, relative to the total proteinaceous matter, of which at least about 26 weight % is in a free form, relative to the total leucine,
   (iii) about 2 g of fat and about 6.2 g of digestible carbohydrates,
for use in the prevention or treatment of a disease or condition which involves muscle decline in a mammal, wherein the nutritional composition is administered as 1 to 2 servings daily, each serving comprising about 150 kcal.

10. The nutritional composition according to claim 1, wherein the mammal is a human of the age of 30 or more.

11. The nutritional composition according to claim 1, wherein the nutritional composition is administered as one serving daily for prevention or as a maintenance dosage.

12. The nutritional composition according to claim 1, wherein the disease or condition is selected from the group of sarcopenia; loss of muscle mass related to aging, during or following body weight maintenance, during or following energy restriction, during or following bed rest, during or following physical trauma treatment (such as fractures) or during or following weightlessness; insufficient muscle protein synthesis; muscle degradation; impaired muscle recovery; muscle damage; muscle proteolysis; muscle atrophy; muscle dystrophy; muscle catabolism; muscle wasting; loss of muscle strength; loss of muscle function; loss of physical capacity; loss of physical performance; impaired mobility; frailty; disability; and risk of falling.

13. A liquid nutritional composition comprising per 100 ml:
   (i) less than 100 kcal of energy,
   (ii) at least about 10 g of proteinaceous matter comprising at least about 80 weight % of whey protein, relative to the total proteinaceous matter, and which comprises at least about 11 weight % of leucine, relative to the total proteinaceous matter, of which at least about 20 weight % is in a free form, relative to the total leucine,
   (iii) a source of fat and a source of digestible carbohydrates,
   (iv) one or more micronutrients selected from the group of carotenoids, vitamin A, calcium, magnesium, vitamin B6, vitamin D3, vitamin C, vitamin E, folic acid, vitamin B12, selenium and zinc.

14. The liquid nutritional composition according to claim 13, comprising per 100 ml, less than 90 kcal of energy.

15. The liquid nutritional composition according to claim 13 comprising per 100 ml:
   (i) about 75 kcal of energy,
   (ii) about 10.5 g of proteinaceous matter comprising about 10 g of whey protein, and comprising about 1.5 g of leucine of which about 0.4 g is in a free form,
   (iii) about 1.5 g of fat and about 4.4 g of digestible carbohydrates, (iv) about 0.15 mg carotenoids, about 75 µg vitamin A, about 375 µg vitamin B6, about 1.5 µg vitamin B12, about 16 mg vitamin C, about 10 µg vitamin D3, about 3.8 mg vitamin E, about 100 µg folic acid, about 7.5 µg selenium, about 1.1 mg zinc, and, (v) optionally, a source of dietary fiber.

16. The liquid nutritional composition according to claim 13, packaged as a 200 ml serving.

17. A solid nutritional composition, comprising per 100 g of dry weight:
(i) less than 500 kcal of energy,
(ii) at least 49 g of proteinaceous matter comprising at least about 80 weight % of whey protein, relative to the total proteinaceous matter, and which comprises at least about 11 weight % of leucine, relative to the total proteinaceous matter, of which at least about 20 weight % is in a free form, relative to the total leucine,
(iii) a source of fat and a source of digestible carbohydrates,
(iv) one or more micronutrients selected from the group of carotenoids, vitamin A, calcium, magnesium, vitamin B6, vitamin C, vitamin D3, vitamin E, folic acid, vitamin B12, selenium and zinc.

18. The solid nutritional composition according to claim 17, comprising per 100 g, less than 445 kcal of energy.

19. The solid nutritional composition according to claim 17, comprising per 100 g of dry weight:
(i) about 375 kcal of energy,
ii) about 52 g of proteinaceous matter which comprises about 50 g of whey protein, and which comprises about 7.5 g of leucine of which about 1.9 g is in a free form,
(iii) about 7.5 g of fat and about 23 g of digestible carbohydrates,
(iv) about 0.75 mg of carotenoids, about 376 µg of vitamin A, about 1.88 mg of vitamin B6, about 80 mg of vitamin C, about 50 µg of vitamin D3, about 18.8 mg of vitamin E, about 500 µg of folic acid, about 7.5 µg of vitamin B12, about 38 µg of selenium, and about 5.5 mg of zinc, and
(v) optionally, a source of dietary fiber.

20. The solid nutritional composition according to claim 17, formed as a powder capable of being dissolved in an aqueous solution.

21. The solid nutritional composition according to claim 17, presented as a serving of about 40 g.

22. The composition according to claim 1, wherein the source of fat comprises omega-3 fatty acids.

23. The nutritional composition according to claim 1, wherein the proteinaceous matter comprises at least about 13 g of proteinaceous matter per 100 kcal.

24. The nutritional composition according to claim 1, wherein the proteinaceous matter comprises at least about 13.5 g of proteinaceous matter per 100 kcal.

25. The nutritional composition according to claim 1, wherein the proteinaceous matter comprises at least about 14 g of proteinaceous matter per 100 kcal.

26. The nutritional composition according to claim 1, wherein the proteinaceous matter comprises at least about 85 weight % of whey protein.

27. The nutritional composition according to claim 1, wherein the proteinaceous matter comprises at least about 90 weight % of whey protein.

28. The nutritional composition according to claim 1, wherein the proteinaceous matter comprises at least about 95 weight % of whey protein.

29. The nutritional composition according to claim 1, wherein the proteinaceous matter comprises at least about 47 weight % of essential amino acids (EAA).

30. The nutritional composition according to claim 1, wherein the proteinaceous matter comprises at least about 50 weight % of essential amino acids (EAA).

31. The nutritional composition according to claim 1, wherein the proteinaceous matter comprises at least about 12.5 weight % of leucine.

32. The nutritional composition according to claim 1, wherein the proteinaceous matter comprises at least about 13 weight % of leucine.

33. The nutritional composition according to claim 1, wherein the proteinaceous matter comprises at least about 14 weight % of leucine.

34. The nutritional composition according to claim 1, wherein the total leucine comprises at least about 26 weight % of leucine in a free form, relative to the total amount of leucine.

35. The nutritional composition according to claim 1, wherein the mammal is a human of the age of 50 or more.

36. The nutritional composition according to claim 1, wherein the mammal is an elderly human.

37. The liquid nutritional composition according to claim 13, comprising per 100 ml, less than 80 kcal of energy.

38. The solid nutritional composition according to claim 17, comprising per 100 g, less than 395 kcal of energy.

39. The composition according to claim 1, wherein the source of fat comprises Eicosapentaenoic Acids.

40. The composition according to claim 1, wherein the source of fat comprises Docosahexaenoic Acids.

* * * * *